(12) United States Patent
Kawamura et al.

(10) Patent No.: US 12,115,278 B2
(45) Date of Patent: Oct. 15, 2024

(54) OVARIAN TISSUE TRANSPLANTATION METHOD AND FOLLICLE ACTIVATION METHOD

(71) Applicant: KITAZATO CORPORATION, Shizuoka (JP)

(72) Inventors: Kazuhiro Kawamura, Tokyo (JP); Yorino Sato, Kanagawa (JP)

(73) Assignee: KITAZATO CORPORATION, Shizuoka (JP)

( * ) Notice: Subject to any disclaimer, the term of this patent is extended or adjusted under 35 U.S.C. 154(b) by 865 days.

(21) Appl. No.: 17/280,189

(22) PCT Filed: Sep. 27, 2019

(86) PCT No.: PCT/JP2019/038351
§ 371 (c)(1),
(2) Date: Mar. 26, 2021

(87) PCT Pub. No.: WO2020/067501
PCT Pub. Date: Apr. 2, 2020

(65) Prior Publication Data
US 2021/0346574 A1    Nov. 11, 2021

(30) Foreign Application Priority Data

Sep. 27, 2018  (JP) ................. 2018-183027

(51) Int. Cl.
*A61B 17/00* (2006.01)
*A61K 9/06* (2006.01)
(Continued)

(52) U.S. Cl.
CPC .......... *A61L 27/3604* (2013.01); *A61K 9/06* (2013.01); *A61K 38/24* (2013.01); *A61L 27/24* (2013.01);
(Continued)

(58) Field of Classification Search
CPC ........................................... A61B 17/425–435
See application file for complete search history.

(56) References Cited

FOREIGN PATENT DOCUMENTS

| JP | 2013526297 A | 6/2013 |
| WO | 2011140428 A1 | 11/2011 |
| WO | 2014043568 A1 | 3/2014 |

OTHER PUBLICATIONS

Itami et al., "Co-culturing of follicles with interstitial cells in collagen gel reproduce follicular development accompanied with theca cell layer formation," Reprod Biol Endocrinol. Dec. 17, 2011; 9:159. (Year: 2011).*

(Continued)

*Primary Examiner* — Thaddeus B Cox
(74) *Attorney, Agent, or Firm* — HAUPTMAN HAM, LLP

(57) ABSTRACT

When transplanting a plurality of ovarian tissue fragments, agglomeration of ovarian tissue fragments is prevented, angiogenesis is promoted, and engraftment rate is improved. When transplanting a plurality of ovarian tissue fragments formed by cutting ovarian tissue into a mammal, and the ovarian tissue fragments are transplanted by an injection step in which collagen gel is injected into a site to be transplanted, using collagen gel with a gel concentration of about 1%, and then a transplantation step in which the plurality of ovarian tissue fragments are inserted into the collagen gel. At this time, each of the plurality of ovarian tissue fragments may be previously encapsulated with the collagen gel.

8 Claims, 14 Drawing Sheets

(51) Int. Cl.
- *A61K 38/24* (2006.01)
- *A61L 27/24* (2006.01)
- *A61L 27/36* (2006.01)
- *A61L 27/44* (2006.01)
- *A61P 15/08* (2006.01)

(52) U.S. Cl.
CPC .......... *A61L 27/3641* (2013.01); *A61L 27/44* (2013.01); *A61P 15/08* (2018.01); *A61B 2017/00969* (2013.01); *A61L 2400/06* (2013.01)

(56) References Cited

OTHER PUBLICATIONS

Henry et al., "Isoform 165 of vascular endothelial growth factor in collagen matrix improves ovine cryopreserved ovarian tissue revascularisation after xenotransplantation in mice," Reproductive Biology and Endocrinology (2015) 13:12. (Year: 2015).*

Katska-Ksiazkiewicz et al., "Genetical and biotechnological methods of utilization of female reproductive potential in mammals," Reprod Biol. 2006; 6 Suppl 1:21-36. (Year: 2006).*

Abir et al., "Pilot study of isolated early human follicles cultured in collagen gels for 24 hours," Human Reproduction, vol. 14, Issue 5, May 1999, pp. 1299â1301. (Year: 1999).*

Fransolet, M., et al., "Influence of mouse strain on ovarian tissue recovery after engraftment with angiogenic factor", Journal of Ovarian Research, 2015, vol. 8, Article No. 14, BioMed Central, 9pp.

Kawamura, K. et al., "Hippo signaling disruption and Akt stimulation of ovarian follicles for infertility treatment", PNAS, Oct. 22, 2013, vol. 110, No. 43, pp. 17474-17479, pp. 1-10, 16pp.

Fransolet, M. et al., "Evaluation of Z-VAD-FMK as an anti apoptotic drug to prevent granulosa cell apoptosis and follicular death after human ovarian tissue transplantation", Journal of Assisted Reproduction and Genetics, Nov. 3, 2018, vol. 36, No. 2, pp. 349-359, Springer Science+Business Media, LLC, 11p.

Labied, S. et al., "Isoform 111 of Vascular Endothelial Growth Factor (VEGF111) Improves Angiogenesis of Ovarian Tissue Xenotransplantation", Transplantation, Feb. 15, 2013, vol. 95, No. 3, pp. 426-433, Lippincott Williams & Wilkins, 8pp.

\* cited by examiner

TRANSPLANTED OVARY WEIGHT
IN hCG ADMINISTERED MICE

*$P < 0.05$.

OVARIAN TISSUE TRANSPLANTATION METHOD AND FOLLICLE ACTIVATION METHOD

RELATED APPLICATIONS

The present application is a National Phase of International Application No. PCT/JP2019/038351 filed Sep. 27, 2019, which claims priority to Japanese Application No. 2018-183027, filed Sep. 27, 2018.

TECHNICAL FIELD

The present invention relates to an ovarian tissue transplantation method and a follicle activation method, and particularly relates to an ovarian tissue transplantation method and a follicle activation method that can prevent agglomeration formation and promote angiogenesis when transplanting a plurality of ovarian tissue fragments.

BACKGROUND ART

The inventor developed a follicle activation therapy that artificially activates primordial follicles remaining in an ovary of a patient who has once undergone menopause and regenerates development of the follicle, thereby enabling the menopausal patient to become pregnant with her own egg. In this method, an ovary is removed laparoscopically, cut into small pieces, and then in vitro cultured, and ovarian tissue fragments are transplanted laparoscopically beneath serosa of Fallopian tubes. Thereafter, follicles develop in the transplanted ovarian tissue, and infertility treatment is performed by in vitro fertilization embryo transplantation after egg collection. (See, for example, Patent Literature 1 and Non Patent Literature 1).

However, there is room for improvement in its therapeutic effect, and in particular, it was necessary to improve engraftment of transplanted ovaries.

Conventionally, ovarian transplantation has been performed not only in the follicle activation therapy bit also in cancer and reproductive medicine. That is, an ovary that has been cryopreserved before chemotherapy, radiation therapy or the like that show egg toxicity is transplanted after the underlying disease has resolved. Unlike the ovary of menopausal patient, the ovary in this case should have a large number of normal follicles in the ovary, and the results of follicle development after ovarian transplantation and treatment results of subsequent in vitro fertilization-embryo transplantation have been expected to be good. However, in reality, the results were not as good as expected from the number of normal follicles, and one of the causes was thought to be poor engraftment rate.

More specifically, ovarian transplantation has so far adopted a method of physically adhering on tissues in the abdominal cavity by a method such as placing or suturing ovarian tissue fragments on retroperitoneum, residual ovary or the like, beneath the serosa of Fallopian tubes. In the follicle activation therapy, autologous transplantation of ovarian tissue fragments in which primordial follicles have been activated are performed laparoscopicaily beneath the serosa of Fallopian tubes and into the ovary. At this time, since a plurality of ovarian tissue fragments are transplanted to a localized place, the plurality of ovarian tissue fragments form an agglomeration.

FIGS. 11 to 13 show examples of ovarian tissue fragment transplantation by a conventional method.

FIGS. 11 and 12 show examples when 1 to 5 mouse ovaries were transplanted independently from each other and when the ovaries of host mice beneath renal capsule were transplanted so as to be in close contact with each other. As a result, when the ovaries were transplanted so as to be in close contact with each other, significant reduction in ovary weight, reduction in ovulation number, further, reduction in the number of mature eggs, and increase in the number of degenerated eggs were observed, as compared with those when the ovaries were transplanted independently from each other. The changes appeared depending on the number of ovaries transplanted so that they were in close contact with each other in a confined space.

In addition, as shown in FIG. 13, when changes in expression of marker genes involved in angiogenesis were examined using the ovaries after transplantation beneath the renal capsule, expression of Hif1 and VEGF induced by ischemia increased, and expression of CD31 that is a marker of endothelial cells constructing a vascular network decreased, thus it was shown that formation of the vascular network was reduced by ischemic.

CITATION LIST

Patent Literature

Patent Literature 1: WO 2014/043568 A

Non Patent Literature

Non Patent Literature 1: Kazuhiro Kawamura et. al. "Proceedings of the National. Academy of Sciences of the United. States of America (PNAS)", Oct. 22, 2013, no. 43, vol. 110, pp. 17474-17479

SUMMARY OF INVENTION

Technical Problem

Promotion of angiogenesis is indispensable for engraftment of ovarian tissue fragments, and it is difficult to promote angiogenesis of transplanted ovarian tissue by conventional methods as shown in the above examples. Once the transplanted ovarian tissue becomes an agglomeration, angiogenesis in the central part of the agglomerates is inhibited, leading to a reduction in engraftment rate.

The present invention has been made in view of such conventional circumstances, and an object of the present invention is, when transplanting a plurality of ovarian tissue fragments, to provide an ovarian tissue transplantation method and a follicle activation method that can prevent agglomeration of the ovarian tissue fragments, promote angiogenesis, and improve the engraftment rate.

Solution to Problem

In order to achieve the above object, the ovarian tissue transplantation method according to the present disclosure includes: an injection step of injecting collagen gel into a site to be transplanted; and then a transplantation step of inserting the plurality of ovarian tissue fragments into the collagen gel.

Further, the ovarian tissue transplantation method according to another disclosure is a method in which a plurality of ovarian tissue fragments formed by cutting the ovarian tissue is transplanted into a mammal, and first, an encapsulation step in which the plurality of ovarian tissue fragments are each encapsulated with collagen gel is performed, and then a step of transplanting the plurality or encapsulated ovarian tissue fragments or a step of injecting collagen gel into a site to be transplanted and then inserting the plurality of encapsulated ovarian tissue fragments into the collagen is performed so that the ovarian tissue fragments are not adhered to each other.

The follicle activation method according to the present disclosure is a follicle activation method for activating follicles in an ovary of mammals including mice and humans, the method including:

(1) a step of removing an ovary from a mammal;
(2) a step of cutting the removed ovary into a plurality of ovarian tissue fragments;
(3) a step of culturing follicles of the ovarian tissue fragments;
(4) a step of injecting collagen gel into a site to be transplanted; and
(5) a step of inserting the plurality of cultured ovarian tissue fragments into the collagen gel.

Further, the follicle activation method according to another disclosure is a follicle activation method for activating follicles in an ovary of mammals including mice and humans, the method including:

(1) a step of removing an ovary from a mammal;
(2) a step of cutting the removed ovary into a plurality of ovarian tissue fragments;
(3) a step of culturing follicles of the ovarian tissue fragments;
(4) a step of encapsulating each of the plurality of cultured ovarian tissue fragments with collagen gel; and
(5) a step of transplanting the plurality of encapsulated ovarian tissue fragments into a patient.

Here, the collagen gel for ovarian tissue transplantation includes human-derived collagen, bovine-derived collagen, and porcine-derived collagen.

Collagen gel is preferably 0.5 to 1 mg/ml of bovine dermis-derived type (pepsin-treated) in the case of Nippi gel, and about 1 to 2% (volume ratio) of phosphate buffer solution in the case of atelocollagen gel (derived from bovine dermis). As a solvent, a coil culture medium can be used, but it is not limited thereto. Also, the volume is preferably 30 to 50 μl, and a collagen gel liquid is injected and then gelled at body temperature.

As a transplantation method, first, each of ovarian tissue fragments (approximately 1 to 2 mm square) is wrapped in collagen gel. Then, at a time when the collagen gel gels to some extent, the entire plurality of ovarian tissue fragments (for example, about 30 fragments in the case of humans) are wrapped with collagen gel, and when the entirety is gelled, transplantation work is performed. This makes it possible to efficiently transplant a plurality of ovarian tissue fragments while the distance between the individual ovarian tissue fragments is maintained by the collagen gel film. Instead of wrapping all ovarian tissue fragments with the collagen gel before transplantation, collagen gel may be first injected into a patient's ovarian fixation position (for example, beneath serosa of Fallopian tubes, residual ovary), and then the individual ovarian tissue fragment may be inserted into the injected collagen gel. After inserting the whole ovarian tissue fragments, the insertion part is slightly squeezed and blended so that the distance between each of the ovarian tissue fragments is sufficiently maintained.

In addition, by using the collagen gel under the above-mentioned conditions, the ovarian tissue fragments can be transplanted without being in close contact with each other at the time of transplanting the ovarian tissue fragment, and moreover, during few days after transplantation, which is the time when angiogenesis is most active, the collagen gel is not completely absorbed into the body, thus it is possible to suppress the adhesion of ovarian tissue fragments and promote angiogenesis until then.

Further, it is preferable to administer human chorionic gonadotropin (hCG) together with the transplantation of the ovarian tissue fragments. The single is set in the range of 5,000 to 10,000 IU, and is administered a predetermined number of times (for example, once) 2 to 3 days after transplantation.

As a method of administration, since hCG acts on the ovary or the endometrium, there is a method of reaching the ovary or the endometrium via systemic blood circulation by injection. However, the method is not limited to this, and higher effects can be also expected by adding hCG to the above collagen and administering it to the ovary, the endometrium, or the vicinity thereof. Of course, it is also possible to use hCG-containing collagen in combination with administration of hCG by injection.

Advantageous Effects of Invention

As described above, according to the present invention, when transplanting a plurality of ovarian tissue fragments, each of the ovarian tissue fragments is encapsulated with collagen gel and transplanted so as not to adhere to each other, whereby it is possible to prevent agglomeration of the ovarian tissue fragments, promote angdogenesis, and improve the engraftment rate. In addition, it can be expected that the engraftment rate will be further increased by a synergistic effect with hCG administration.

DESCRIPTION OF EMBODIMENTS

Figure 1:
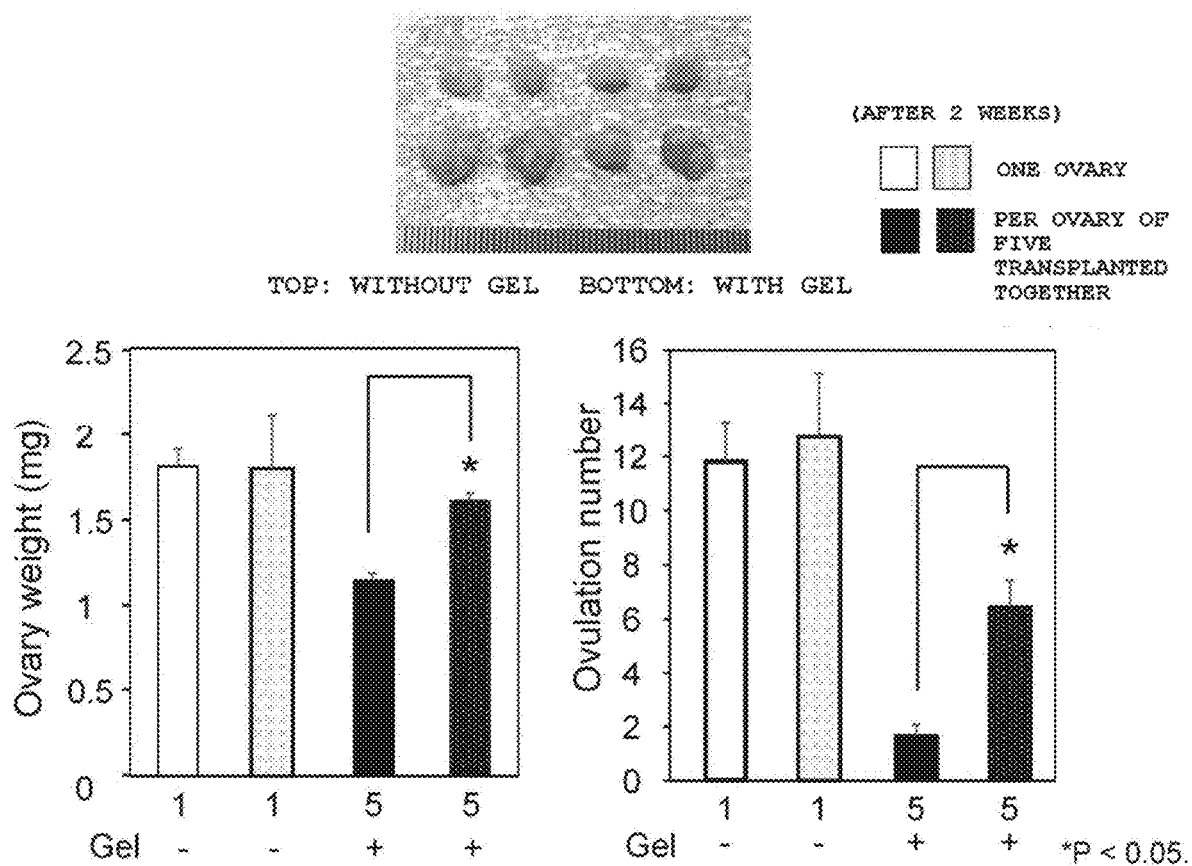
FIG. 1 is an explanatory diagram of an effect of Example 1 of the present invention, and is a graph showing ovulation weight and ovulation number according to the presence or absence of collagen gel encapsulation.

Hereinafter, embodiments of the ovarian tissue transplantation method and the follicle activation method according to the present invention will be described. The inventor considered that poor engraftment rate of transplanted ovarian tissue was caused by the transplanted ovarian tissue fragments adhering to each other and hindering angiogenesis, and tested a hypothesis using animal tests.

Ovary weight and ovulation number per ovary 2 weeks after transplantation were compared between a group in which five mouse ovaries were transplanted together beneath renal capsule and a group in which five were each separately transplanted beneath the renal capsule.

In addition, expression levels of angiogenesis markers Hif1, VEGF, and CD31 in the transplanted ovaries were measured in each group, From these research results, it was clarified that when the ovaries are transplanted together so that the transplanted ovaries are in close contact with each other, the ovary weight is remarkably reduced and the ovulation number is reduced. In addition, it was suggested that, from changes in gene expression of angiogenic factors, high-density transplantation causes ovarian ischemia and compensates for an increase in VEGF, but the effect is insufficient and angiogenesis is prominently reduced.

Therefore, in order to improve the engraftment rate of the transplanted ovaries, the transplanted ovarian tissue fragments are encapsulated with collagen gel at the time of transplantation so as not to adhere to each other, and transplanted so as not to adhere to each other, the ovary weight, changes in expression of angiogenic factors, the ovulation number, and follicle number at each follicle stage were measured to evaluate whether or not gel combined use ovarian transplantation was useful.

VEGF is an important factor that induces angiogenesis, but from the above experimental results, it is considered that the production amount of VEGF induced is insufficient to actually induce angiogenesis.

Therefore, direct administration of VEGF is considered to be effective for inducing angiogenesis, but problems are that VEGF has a short half life and requires frequent administration, and VEGF does not exist as a drug that can be directly administered to humans.

Human chorionic gonadotropin (hCG), which is used to induce ovulation during infertility treatment, has a long half-life, is known to act on ovarian granulosa cells to promote VEGF expression for a long period of time, and may cause ovarian hyperstimulation syndrome.

Therefore, it was verified whether administration of hCG before ovarian tissue transplantation could increase endogenous VEGF and improve angiogenic disorders due to ischemia. At this time, since many diseases have almost no granulosa cells in the ovary, the endometrium was proposed as a VEGF production site other than the ovary, and the effect was evaluated.

Example 1

FIG. 1 to FIG. 3

In this example, the transplanted ovarian tissue fragments were encapsulated with collagen gel at the time of transplantation so as not to adhere to each other, and then transplanted so as not to adhere to each other, and the effect was evaluated.

Conditions of the collagen gel used in this example are as follows.

Product name: Collagen gel
Component: Dissolved in bovine dermis-derived type I (acid-treated) MEM.
Gel concentration (final): 1%
Gel formation amount (amount to be added at the time of transplantation): 30 to 50 µl By injecting the above collagen gel beneath renal capsule of a mouse with a syringe with a needle and then inserting an ovary into the site, a state in which the ovary was encapsulated with the gelled collagen gel was created.

When ovary weight and ovulation number were measured 2 weeks after transplantation, the ovary weight recovered 1.5 times and the ovulation number tripled as compared with control without gel (FIG. 1).

Figure 2:
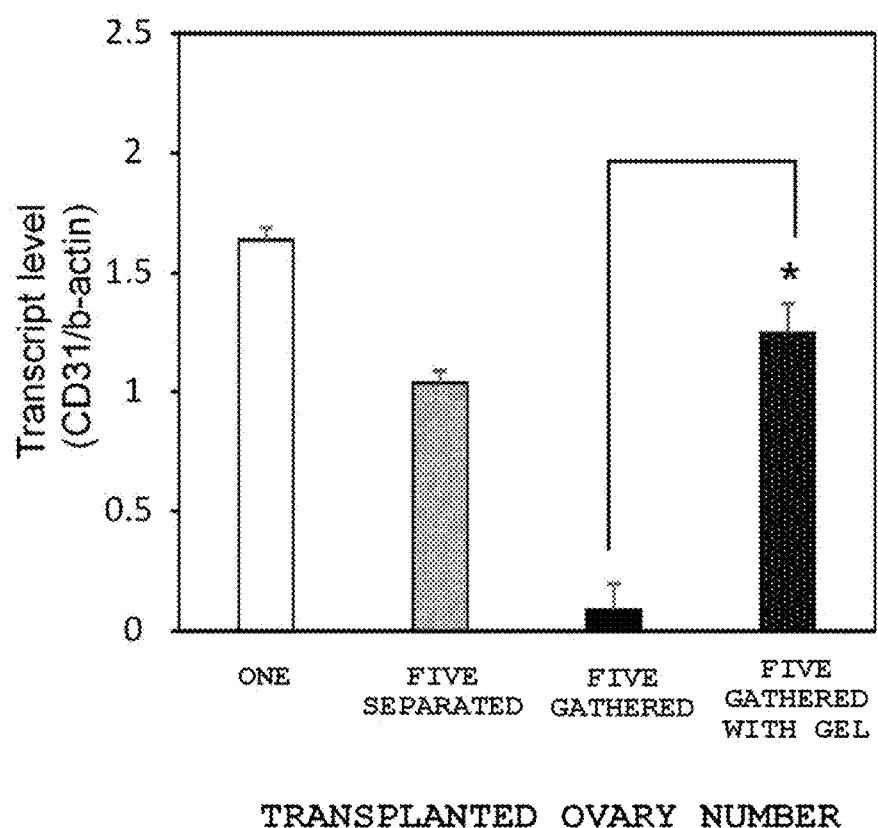
FIG. 2 is an explanatory diagram of an effect of Example 1 of the present invention, and is a graph showing CD31 gene expression level according to the presence or absence of collagen gel encapsulation.

Furthermore, when gene expression of CD31 in the ovary was examined, the expression level was significantly increased in the gel combined use transplanted ovary, indicating that vascular network formation was recovered (FIG. 2).

Figure 3:
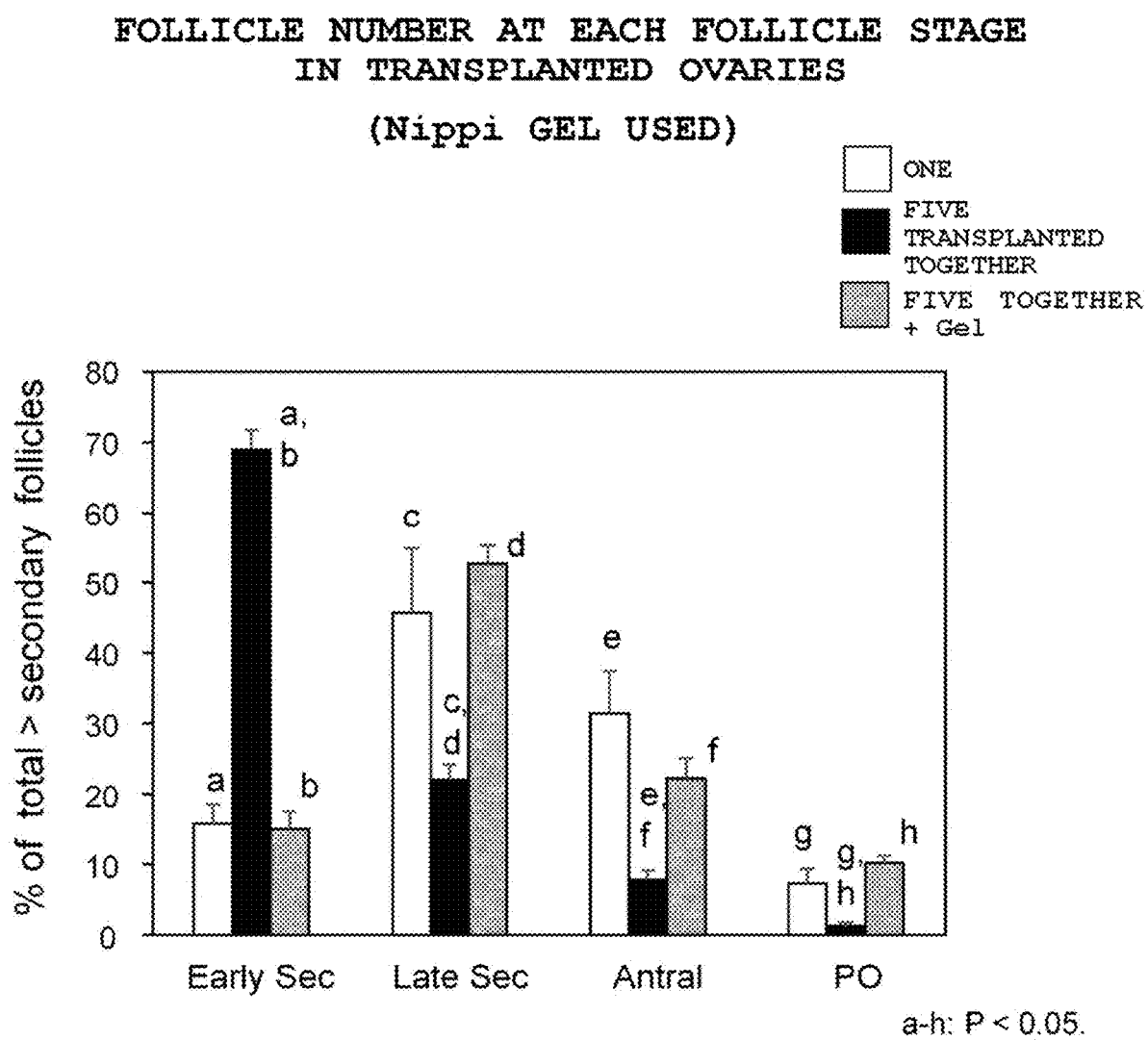
FIG. 3 is an explanatory diagram of an effect of Example 1 of the present invention, and is a graph showing a ratio of follicle number (of total>secondary follicles) at each follicle stage of secondary follicles and later according to the presence or absence of collagen gel encapsulation.

In addition, when follicles at each developmental stage after a second follicular phase in the transplanted ovary were measured, follicle numbers in late secondary follicle (Late Sec), vesicular follicle (Antral) and preovulatory follicle (PO) were increased to almost the same number as control (one transplanted with intervals), indicating that follicle development was improved (FIG. 3).

Example 2

FIG. 4, FIG. 5

Figure 4:
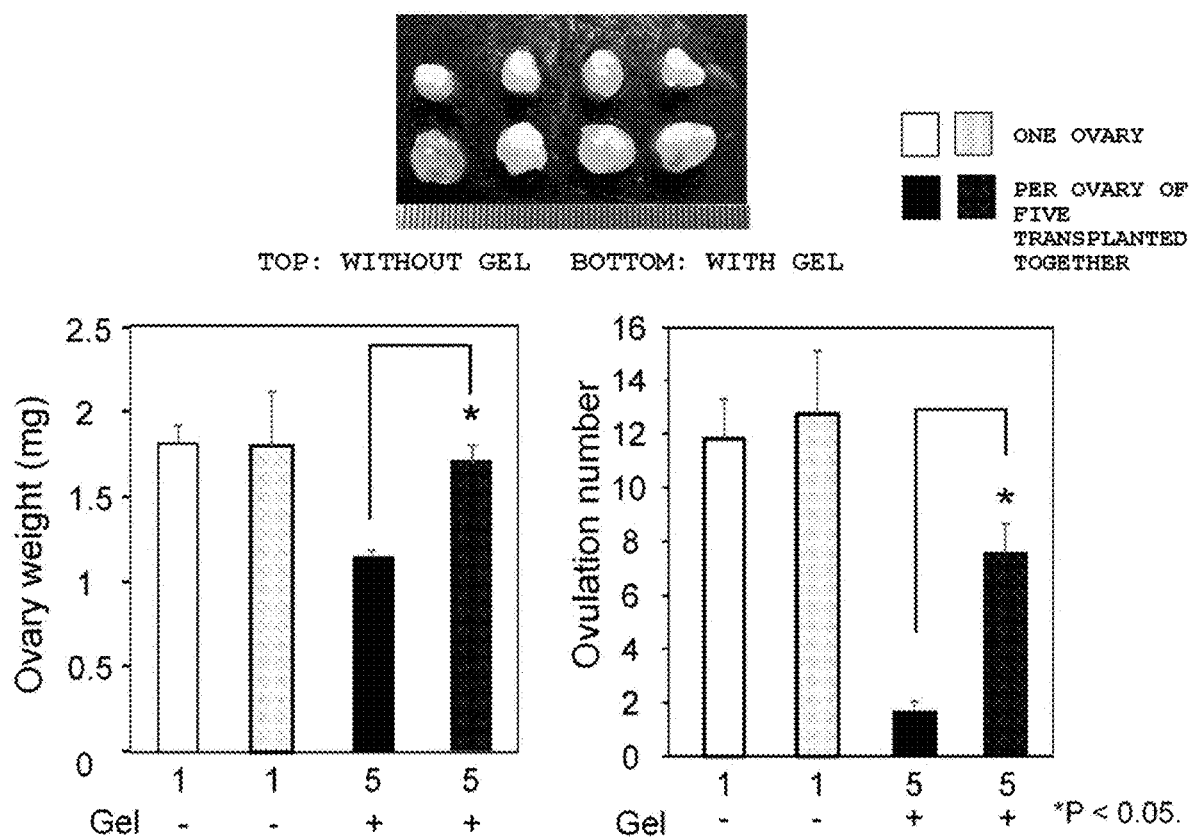
FIG. 4 is an explanatory diagram of an effect of Example 2 of the present invention, and is a graph showing ovary weight and ovulation number according to the presence or absence of collagen gel encapsulation.
Figure 5:
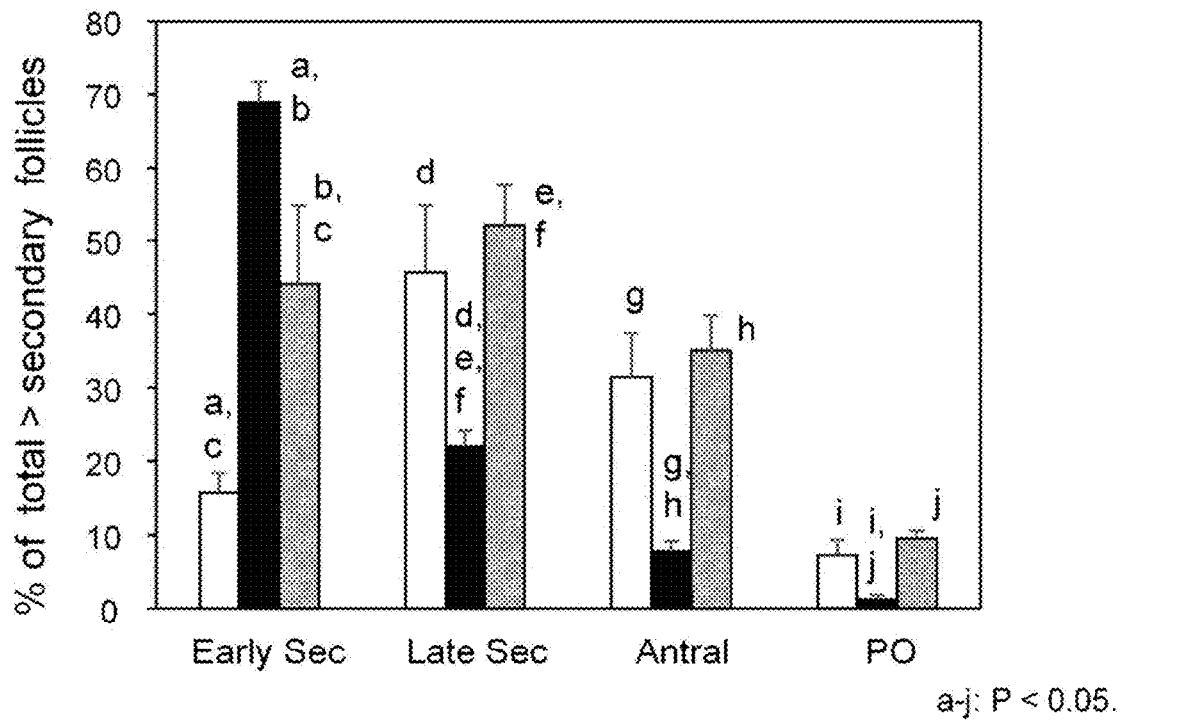
FIG. 5 is an explanatory diagram of an effect of Example 2 of the present invention, and is a graph showing a ratio of follicle number (of total>secondary follicles) at each follicle stage of secondary follicles and later according to the presence or absence of collagen gel encapsulation.

Experiments were carried out under the same conditions as in Example 1, using atelocollagen gel which was permitted to be injected into a human body. As a result, it was shown that engraftment of the transplanted ovary was improved as in Example 1 also when the atelocollagen gel was used (FIG. 4, FIG. 5).

Product name: Koken Atelocollagen Implant.

Component: 1% Atelocollagen (derived from bovine dermis) phosphate buffer solution Gel concentration (final): 1%

Gel formation amount (amount to be added at the time of transplantation): 30 to 50 µl As described above, good results were obtained for ovarian transplantation in Examples 1 and 2. However, in an experiment conducted using Corning High Concentration (HC) Matrigel matrix Growth Factor Reduced (Corning, Matrigel is a registered trademark of Corning Inc., USA), components: laminin 61%, collagen IV 30%, and entactin 1%, as collagen gel, the ovary could not be inserted into the transplant site because hardness at the time of gel formation was too loose.

In addition, experiments were conducted using agarose gel, component: agarose, instead of collagen gel, for gel concentrations of 0.1%, 0.5%, 1.0%, and 1.5%, respectively. However, the gel hardness was too loose to be inserted into the transplant site at concentrations at the time of gel formation of 0.1% and 0.5%, and the gel hardness was too hard to encapsulate a graft after insertion at concentrations of 1.0% and 1.5%.

Example 3

FIG. 6, FIG. 7

Next, effects of hCG on angiogenesis of transplanted ovaries were verified. One or five mouse ovaries were transplanted together beneath ovarian renal capsule of host mice so that they were in close contact with each other. In addition, 5 IU hCG was administered to the mouse into which five ovaries were transplanted so as to be in close contact with each other 1 hour after ovarian transplantation.

Figure 6:
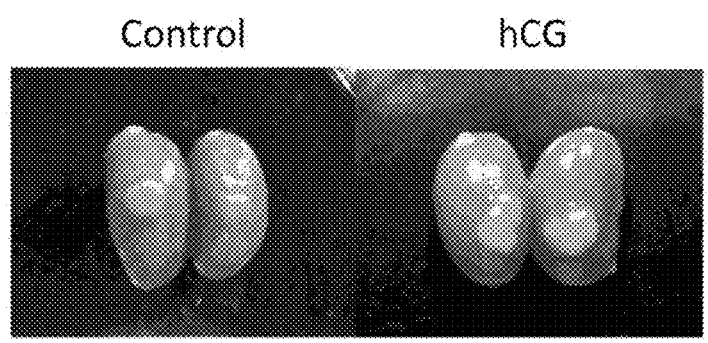
FIG. 6 is an explanatory diagram of an effect of Example 3 of the present invention, and is a graph showing ovary weight and ovulation number according to the presence or absence of hCG administration beneath ovarian renal capsule.
Figure 6:
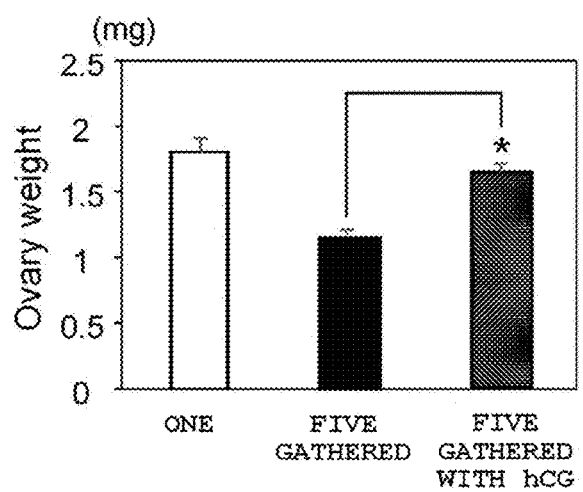
Figure 6:
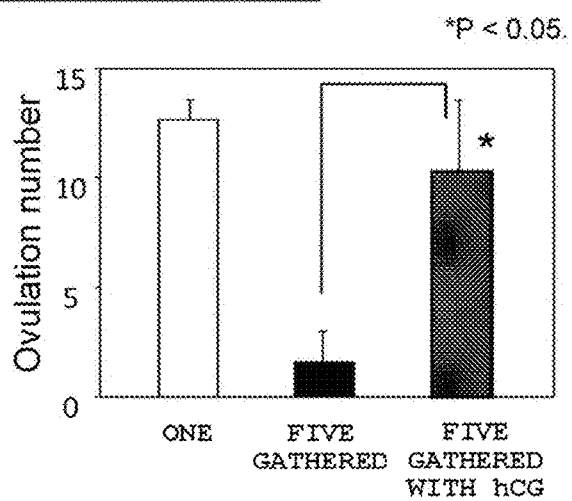

Ovary weight and ovulation number per ovary 2 weeks after transplantation were significantly increased in the hCG-administered group (FIG. 6).

Figure 7:
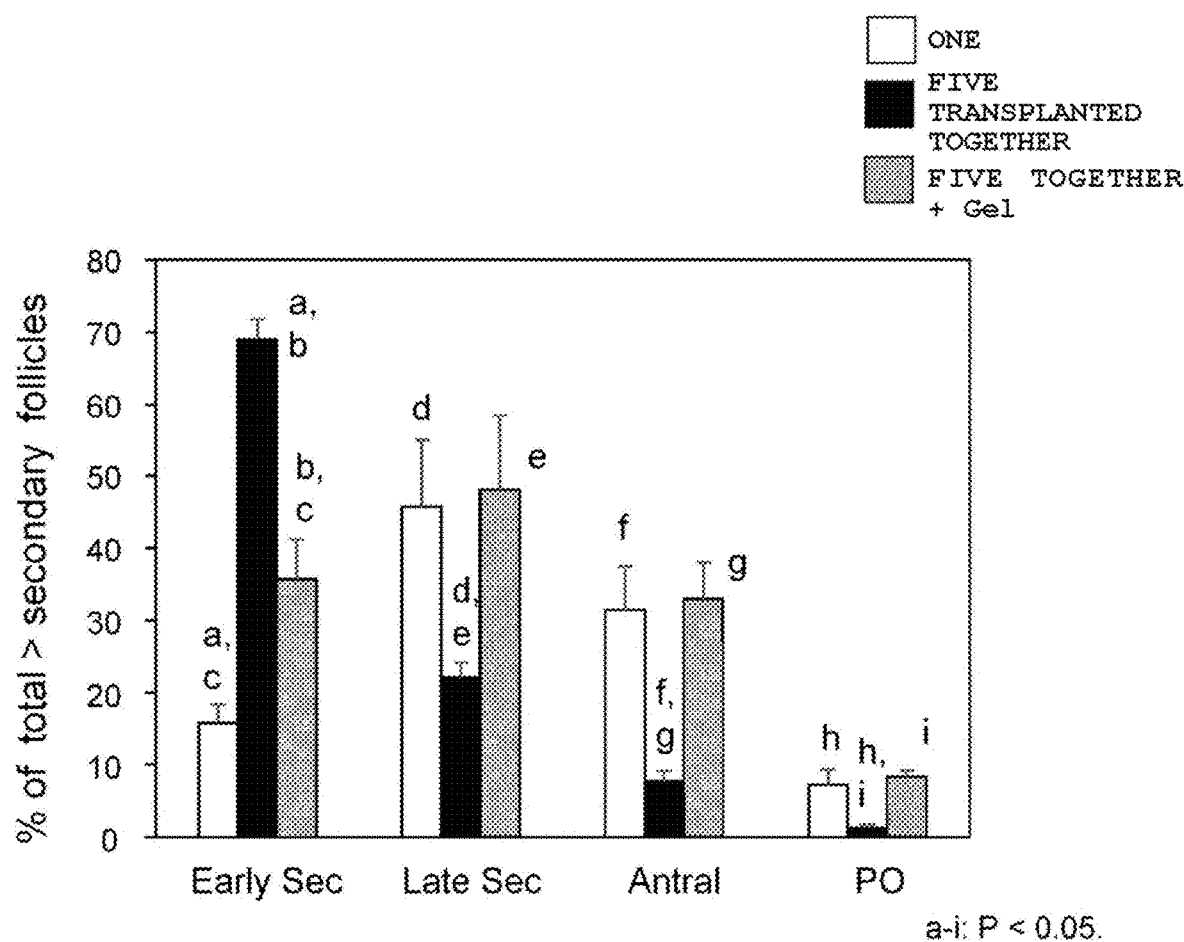
FIG. 7 is an explanatory diagram of an effect of Example 3 of the present invention, and is a graph showing a ratio of follicle number (of total>secondary follicles) at each follicle stage of secondary follicles and later according to the presence or absence of hCG administration beneath the ovarian renal capsule.

In addition, when the transplanted ovaries were collected from the mice administered with hCG after ovarian transplantation, and follicle numbers at each developmental stage after the second follicular phase were measured, late secondary follicles (Late Sec), vesicular follicles (Antral) and preovulatory follicles (PO) were increased, indicating that follicle development was improved (FIG. 7).

Example 4

FIG. 8, FIG. 9

Figure 8:
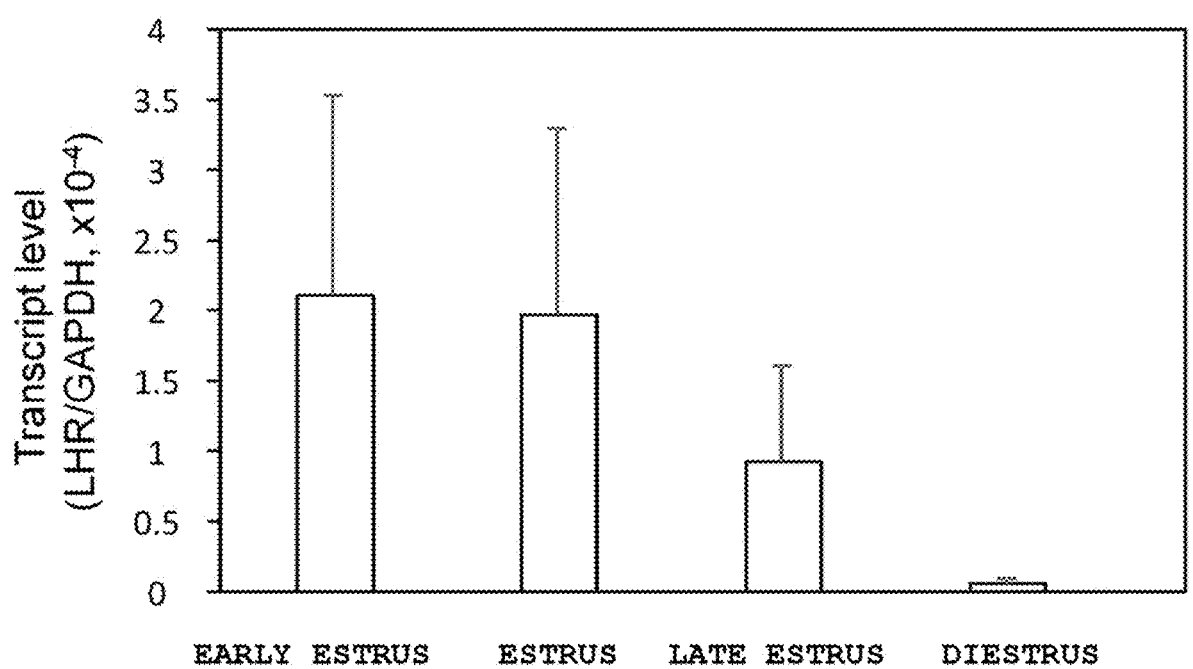
FIG. 8 is an explanatory diagram of an effect of Example 4 of the present invention, and is a graph showing LHR gene expression level in each sexual cycle in uterus.
Figure 9:
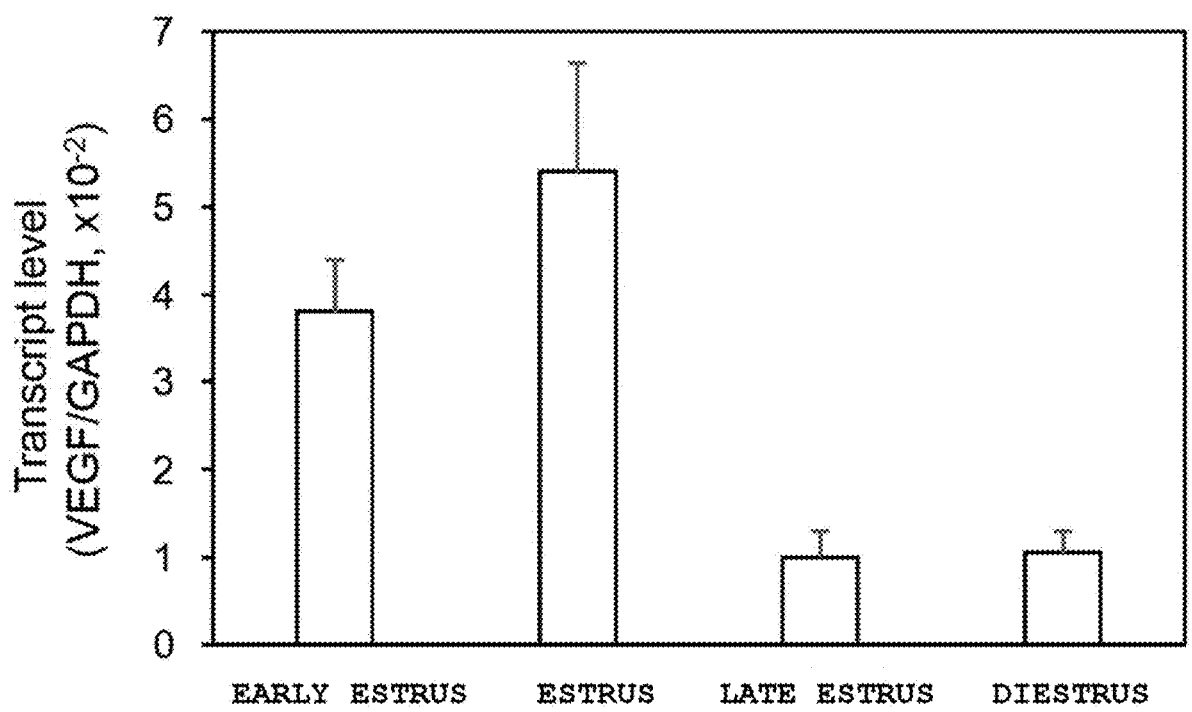
FIG. 9 is an explanatory diagram of an effect of Example 4 of the present invention, and is a graph showing VEGF gene expression level in each sexual cycle in the uterus.

Furthermore, induction of VEGF expression by hCG in the endometrium was attempted with an aim of developing a method that would be useful for all patients. The mouse uterus also expresses an hCG receptor (LHR), and its expression level in each sexual cycle was high in early estrus and estrus, decreased from late estrus, and hardly expressed in diestrus (FIG. 8). Also, induction of VEGF expression of the uterus by hCG correlated with the expression level of LHR and showed high values in early estrus and estrus (FIG. 9).

Example 5

FIG. 10

Figure 10:
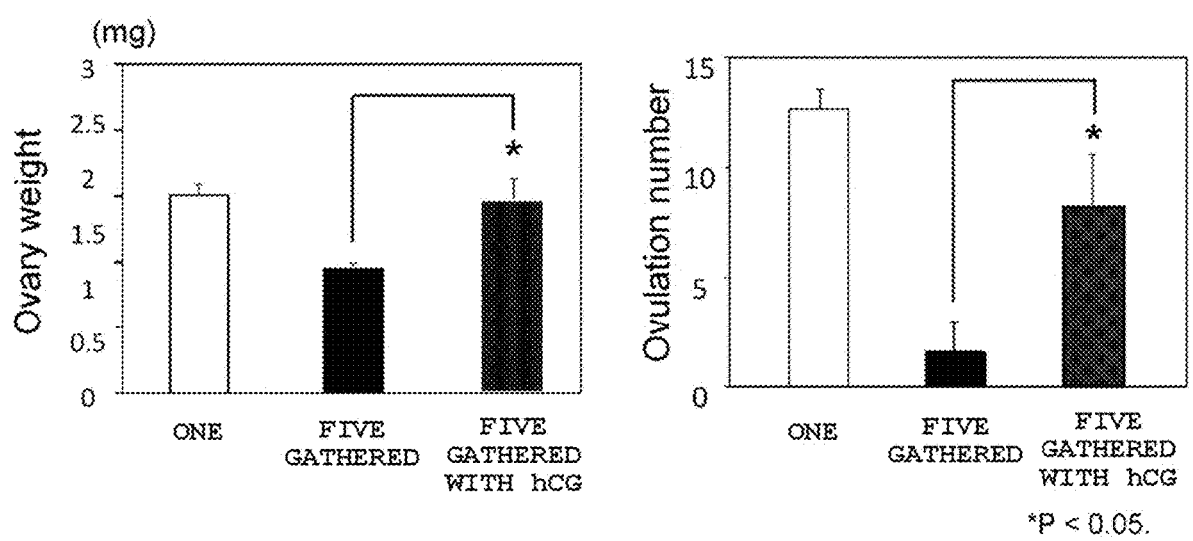
FIG. 10 is an explanatory diagram of an effect of Example 5 of the present invention, and is a graph showing ovary weight and ovulation number according to the presence or absence of hCG administration in uterus.
Figure 11:
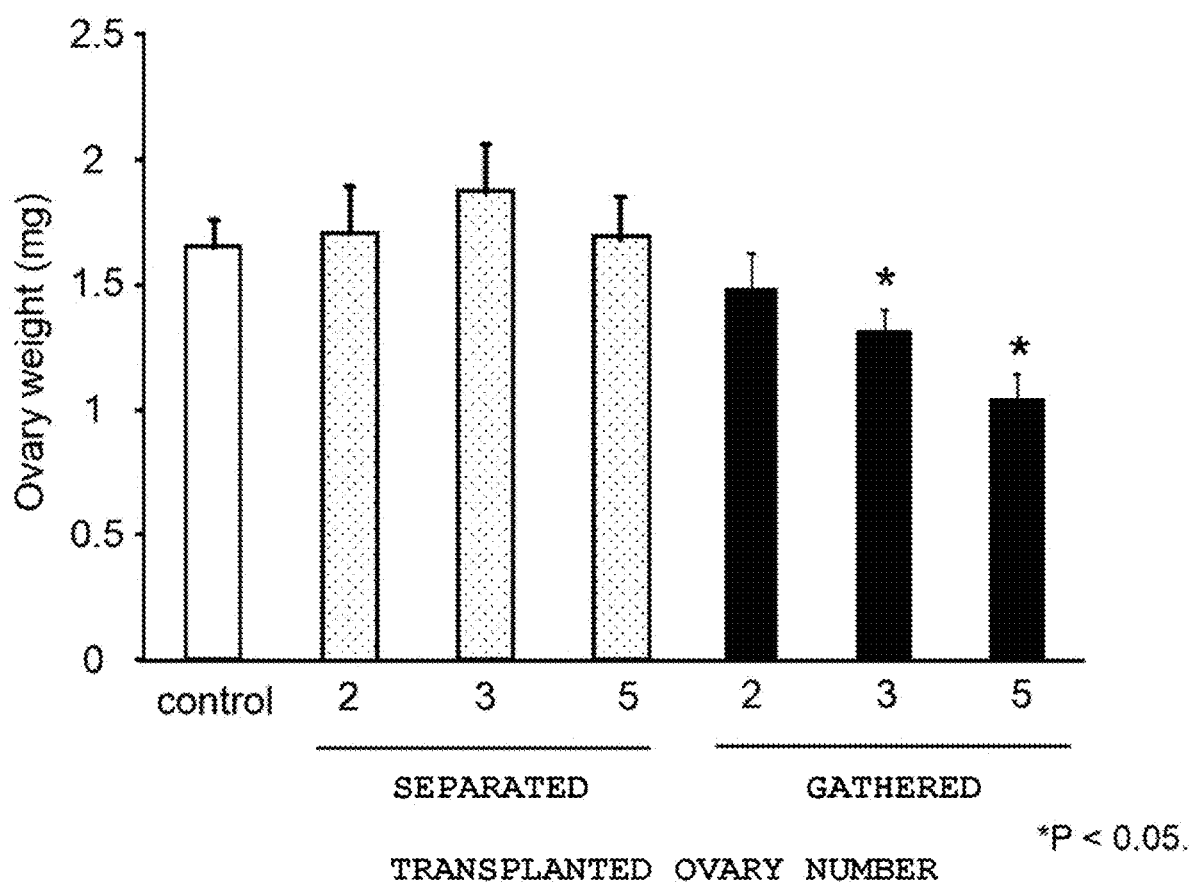
FIG. 11 is a graph showing ovary weight when ovaries are transplanted separately and when transplanted together according to comparative examples.
Figure 12:
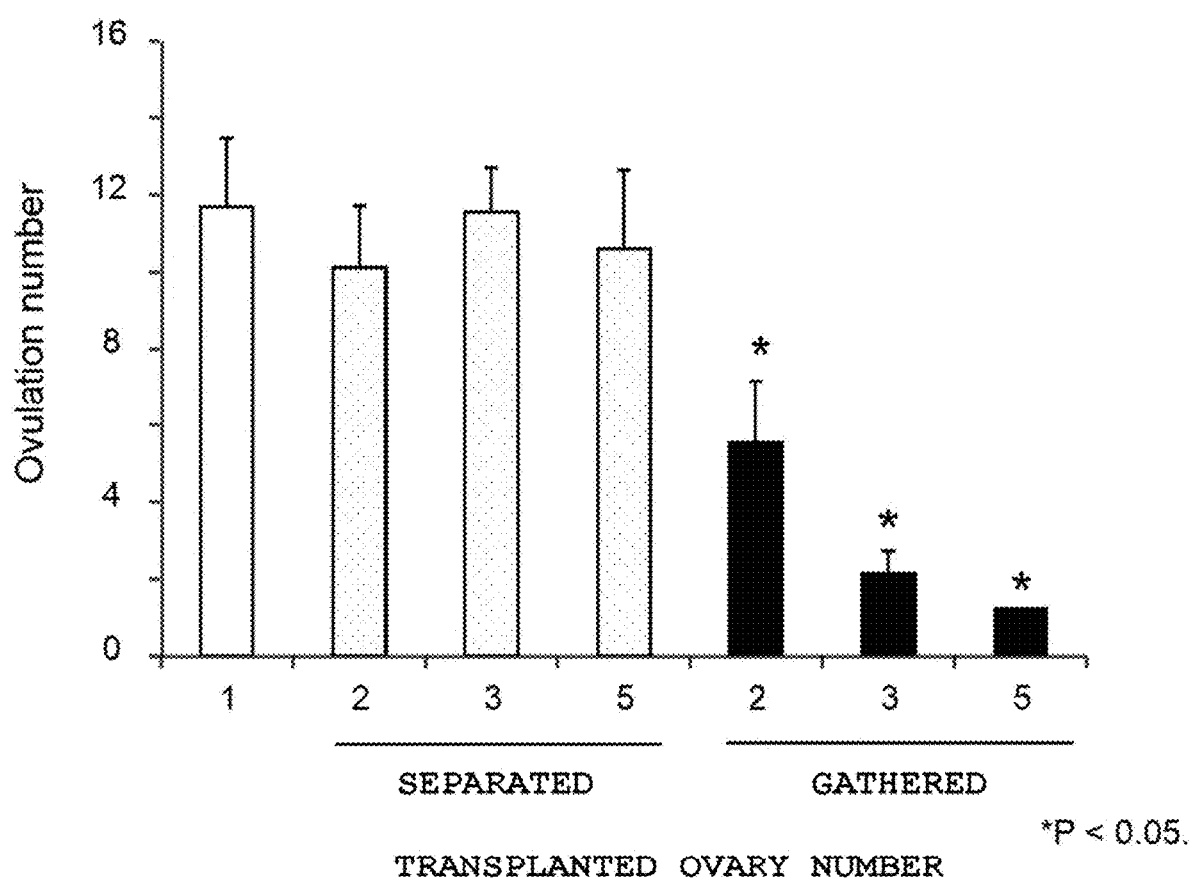
FIG. 12 is a graph showing ovulation number when the ovaries are transplanted separately and when transplanted together according to comparative examples.
Figure 13:
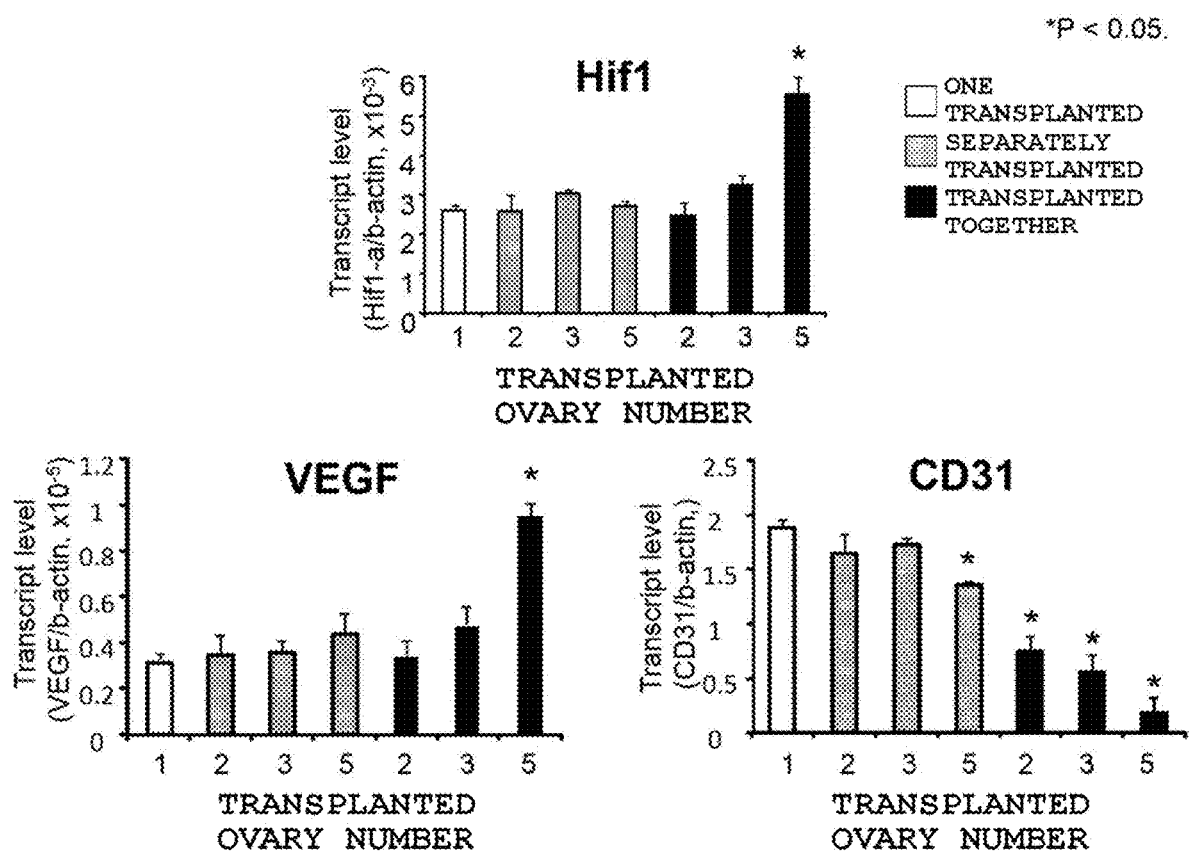
FIG. 13 is a graph showing changes in gene expression of angiogenic factors when the ovaries are transplanted separately and when transplanted together according to comparative examples.
Figure 14:
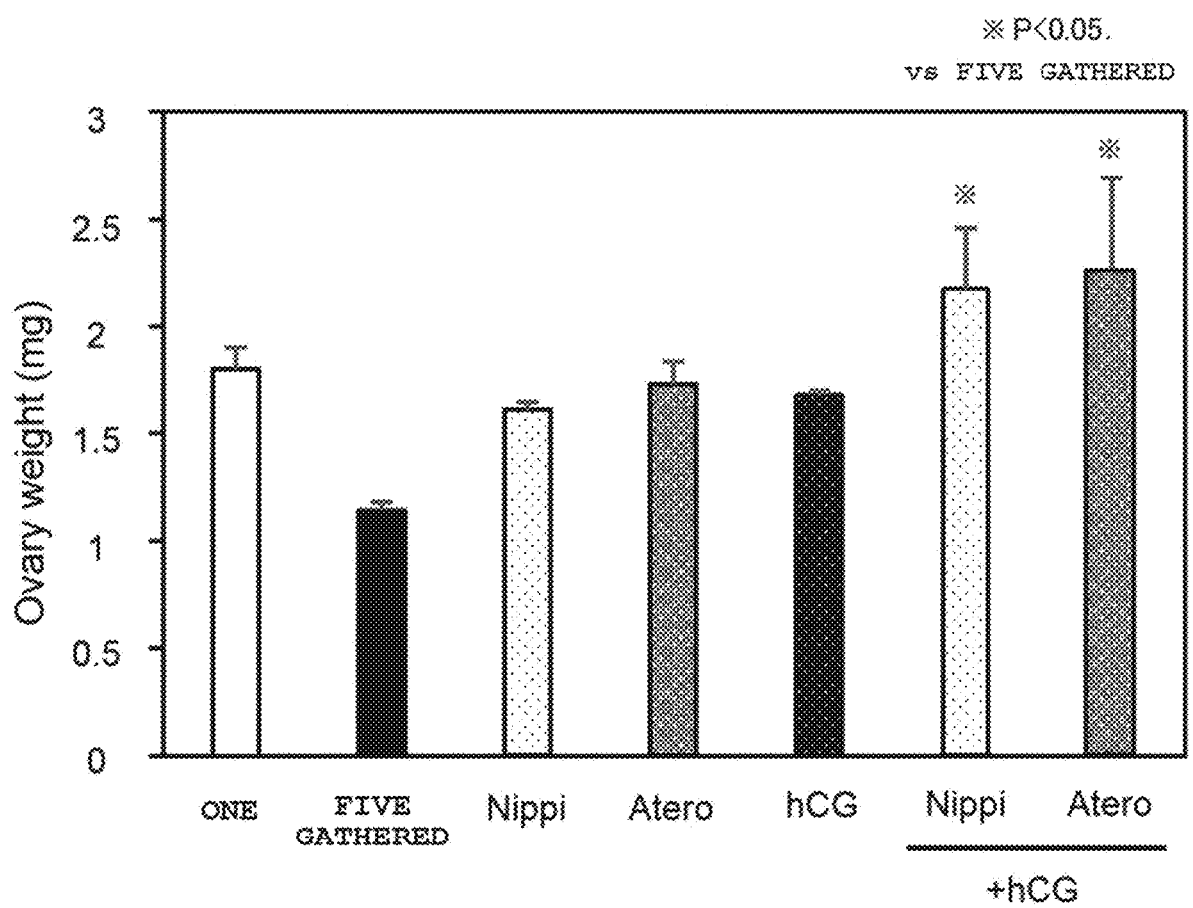
FIG. 14 is a graph showing ovary weight according to the presence or absence of collagen gel encapsulation or hCG administration when ovaries are transplanted together, and when collagen gel encapsulation and hCG administration are used in combination, according to Example 5 of the present invention.

In order to investigate effects of induction of VEF expression by hCG in the uterus on engraftment of the transplanted ovaries, one or five ovaries were transplanted into host mice from which ovaries were removed in estrus so that they were in close contact with each other, and hCG was administered after transplantation. As a result, ovary weight and the number of mature eggs per ovary 2 weeks after transplantation increased significantly in the hCG-administered group (FIG. 10). Further, when gel and hCG administration were used in combination, the ovary weight increased compared to single use groups (FIG. 14).

In each of the above examples, collagen gel was first injected into an ovarian fixation position (site to be transplanted), and then a plurality of ovarian tissue fragments (approximately 1 to 2 mm square) were inserted into the injected collagen gel. As a result, each of the ovarian tissue fragments was dispersed in the injected collagen gel, and each of the ovarian tissue fragments could be transplanted without being in close contact with each other. Preferably, the collagen gel is spread out or the insertion part is slightly squeezed and blended until the collagen gel sets to some extent and the ovarian tissue fragment becomes almost immobile.

First, each of the ovarian tissue fragments is encapsulated with collagen gel to be gelled, and then the collagen gel may be injected into the ovarian fixation position, followed by inserting the individual encapsulated ovarian tissue fragments into the injected collagen gel. As a result, each of the encapsulated ovarian tissue fragments keeps a certain distance in the injected collagen gel, so that it is possible to efficiently prevent the ovarian tissue fragments from adhering and save labor in transplantation work.

Incidentally, the same effect can be expected even if the entirety of individual ovarian tissue fragments previously encapsulated with collagen gel is wrapped with collagen gel, and at a time when the entirety is gelled, a plurality of ovarian tissue fragments covered with the collagen gel are transplanted once or in several times. However, it is preferable to previously inject the collagen gel into the ovarian fixation position and then insert individual ovarian tissue fragments into the collagen gel through an incision for injecting the collagen gel because the size of the incision does not have to be changed.

As described above, according to the present embodiment, encapsulation of the transplanted ovary with collagen gel and administration of hCG at the time of ovarian transplantation can improve angiogenesis in the transplanted ovary and improve ovarian engraftment.

For a detailed discussion of the follicle activation method, see Patent Literature 1 and Non Patent Literature 1 above, all of which are incorporated herein by reference.

The invention claimed is:

1. An ovarian tissue transplantation method in which a plurality of ovarian tissue fragments formed by cutting ovarian tissue is transplanted into a mammal, the method comprising: an injection step of injecting collagen gel into a site to be transplanted; and then a transplantation step of inserting the plurality of ovarian tissue fragments into the collagen gel.

2. The ovarian tissue transplantation method according to claim 1, further comprising a step of administering human chorionic gonadotropin in the range of 5,000 to 10,000 IU after the transplantation step.

3. The ovarian tissue transplantation method according to claim 1, wherein the collagen gel contains 5,000 to 10,000 IU of human chorionic gonadotropin as a whole.

4. An ovarian tissue transplantation method in which a plurality of ovarian tissue fragments formed by cutting ovarian tissue is transplanted into a mammal, the method comprising: an encapsulation step of encapsulating each of the plurality of ovarian tissue fragments with collagen gel; and then a transplantation step of transplanting the plurality of encapsulated ovarian tissue fragments, wherein the transplantation step includes injecting collagen gel into a site to be transplanted, and then inserting the plurality of ovarian tissue fragments encapsulated in the encapsulation step into the collagen gel.

5. An ovarian tissue transplantation method in which a plurality of ovarian tissue fragments formed by cutting ovarian tissue is transplanted into a mammal, the method comprising: an encapsulation step of encapsulating each of the plurality of ovarian tissue fragments with collagen gel; and then a transplantation step of transplanting the plurality of encapsulated ovarian tissue fragments, wherein the encapsulation step includes, after the collagen gel encapsulating each of the plurality of ovarian tissue fragments is gelled, further encapsulating an entirety of the plurality of encapsulated ovarian tissue fragments with collagen gel.

6. A follicle activation method for activating follicles in an ovary of mammals, the method comprising:
(1) a step of removing an ovary from a mammal;
(2) a step of cutting the removed ovary into a plurality of ovarian tissue fragments;
(3) a step of culturing follicles of the ovarian tissue fragments;
(4) a step of injecting collagen gel into a site to be transplanted; and
(5) a step of inserting the plurality of cultured ovarian tissue fragments into the collagen gel.

7. A follicle activation method for activating follicles in an ovary of mammals, the method comprising:
(1) a step of removing an ovary from a mammal;
(2) a step of cutting the removed ovary into a plurality of ovarian tissue fragments;
(3) a step of culturing follicles of the ovarian tissue fragments;
(4) a step of encapsulating each of the plurality of cultured ovarian tissue fragments with collagen gel; and
(5) a step of transplanting the plurality of encapsulated ovarian tissue fragments into a patient, wherein the step (5) includes injecting collagen gel into a site to be transplanted, and then inserting the ovarian tissue fragments encapsulated in the step (4) into the injected collagen gel.

8. An ovarian tissue transplantation method in which a plurality of ovarian tissue fragments formed by cutting ovarian tissue is transplanted into a mammal, the method comprising: an encapsulation step of encapsulating each of the plurality of ovarian tissue fragments with collagen gel; and then a transplantation step of transplanting the plurality of encapsulated ovarian tissue fragments, wherein the collagen gel contains 5,000 to 10,000 IU of human chorionic gonadotropin as a whole.

* * * * *